United States Patent [19]

Pansiera

[11] Patent Number: 4,928,676
[45] Date of Patent: May 29, 1990

[54] KNEE BRACE WITH FLEXIBLE SECONDARY JOINT

[76] Inventor: Timothy Pansiera, 1050 N.W. First Ave., Boca Raton, Fla. 33432

[21] Appl. No.: 315,760

[22] Filed: Feb. 27, 1989

[51] Int. Cl.⁵ .................................................. A61F 5/04
[52] U.S. Cl. ................................. 128/80 F; 128/80 C
[58] Field of Search ........................ 128/80 C, 80 F, 88

[56] References Cited

U.S. PATENT DOCUMENTS

| | | | |
|---|---|---|---|
| 401,933 | 4/1889 | Camp | 128/88 |
| 1,851,241 | 3/1932 | Dresser | 128/80 F |
| 3,316,900 | 5/1967 | Young | 128/80 F |
| 3,350,719 | 11/1967 | McClure, Jr. | 128/80 R |
| 3,827,431 | 8/1974 | Pecorella | 128/80 F |
| 3,923,047 | 12/1975 | Chant | 128/88 |
| 4,249,524 | 2/1981 | Anderson | 128/80 C |
| 4,337,764 | 7/1982 | Lerman | 128/80 F |
| 4,493,316 | 1/1985 | Reed et al. | 128/80 C |
| 4,502,472 | 3/1985 | Pansiera | 128/80 F |
| 4,520,802 | 6/1985 | Mercer et al. | 128/80 C |
| 4,554,913 | 11/1985 | Womack et al. | 128/80 C |
| 4,718,665 | 1/1988 | Airy et al. | 128/88 |

FOREIGN PATENT DOCUMENTS 8300283 2/1983 World Int. Prop. O. ............ 128/88

*Primary Examiner*—Edgar S. Burr
*Assistant Examiner*—Tonya Lamb
*Attorney, Agent, or Firm*—M. K. Silverman

[57] ABSTRACT

There is provided a knee brace having a primary joint and a flexible secondary joint. The brace permits a more natural flexibility of the knee and lower leg, both when the lower leg is co-linear with the upper leg and when the lower leg is bent relative to the upper leg, as in the case during the sitting.

5 Claims, 3 Drawing Sheets

KNEE BRACE WITH FLEXIBLE SECONDARY JOINT

BACKGROUND OF THE INVENTION

A long standing problem in the area of knee braces has resided in the fact that the lower portion of the knee brace is generally excessively rigid relative to the upper portion, and the function of prior art knee braces does not approximate that of the human knee. The present invention seeks to respond to this problem by providing a leg brace in which the lower member (the portion below the knee) may, selectively, be provided with a controllable lower leg extension assist and arc of movement, relative to the upper member of the brace.

There does, to the knowledge of the Inventor, exist relevant prior art only in my own U.S. Pat. No. 4,502,472 (1985), entitled Hinge Mean for Orthopedic Brace and in presently available braces, that apply a constant extension force to the lower leg without, however, means to disengage the extension force upon the occurrence of flexion.

SUMMARY OF THE INVENTION

The present invention constitutes a knee brace having a primary joint and a flexible secondary joint. The inventive brace includes an upper support member for support of the lateral side of the leg above the knee, said upper member having an upper end and a lower end. Further included is a lower support member for support of said lateral side of the leg below the knee, said lower member having an upper end and a lower end. Further provided is a bi-axial element having a primary axis and a secondary axis, said lower end of said upper member being rotationally coupled to said primary axis, said upper end of said lower member being rotationally coupled to said secondary axis. Yet further provided is lock means for selectively locking said lower end of said upper member to said primary axis, thereby selectably overriding said rotational coupling between said upper member and said primary axis of said bi-axial element. Therein, actuation of said locking means operates to change the effective axis of said bi-axial element from said primary axis to the secondary axis. Yet further provided in the inventive brace is a mechanical damping means secured within said upper end of said lower member, and applied said against secondary axis to thereby control the rotational characteristic of said rotational coupling between said secondary axis and said upper end of said lower member.

It is, accordingly, an object of the above knee brace to provide a resultant system that will permit a more natural gate of the user during ambulation when the lower part of the leg is in line with the upper part thereof and when the lower part of the leg is bent relative to the upper part thereof, as is the case when sitting.

It is another object to provide a knee brace having a joint with two axes in proximity to the anatomic axis of the knee in which one axis will afford complete range of motion and the second axis, when used, will effect an assisted extension of the lower leg.

The above and yet other objects and advantages of the present invention will become apparent from the hereinafter set forth Detailed Description of the Invention, the Drawings, and Claims appended herewith.

DETAILED DESCRIPTION OF THE INVENTION

Figure 1:
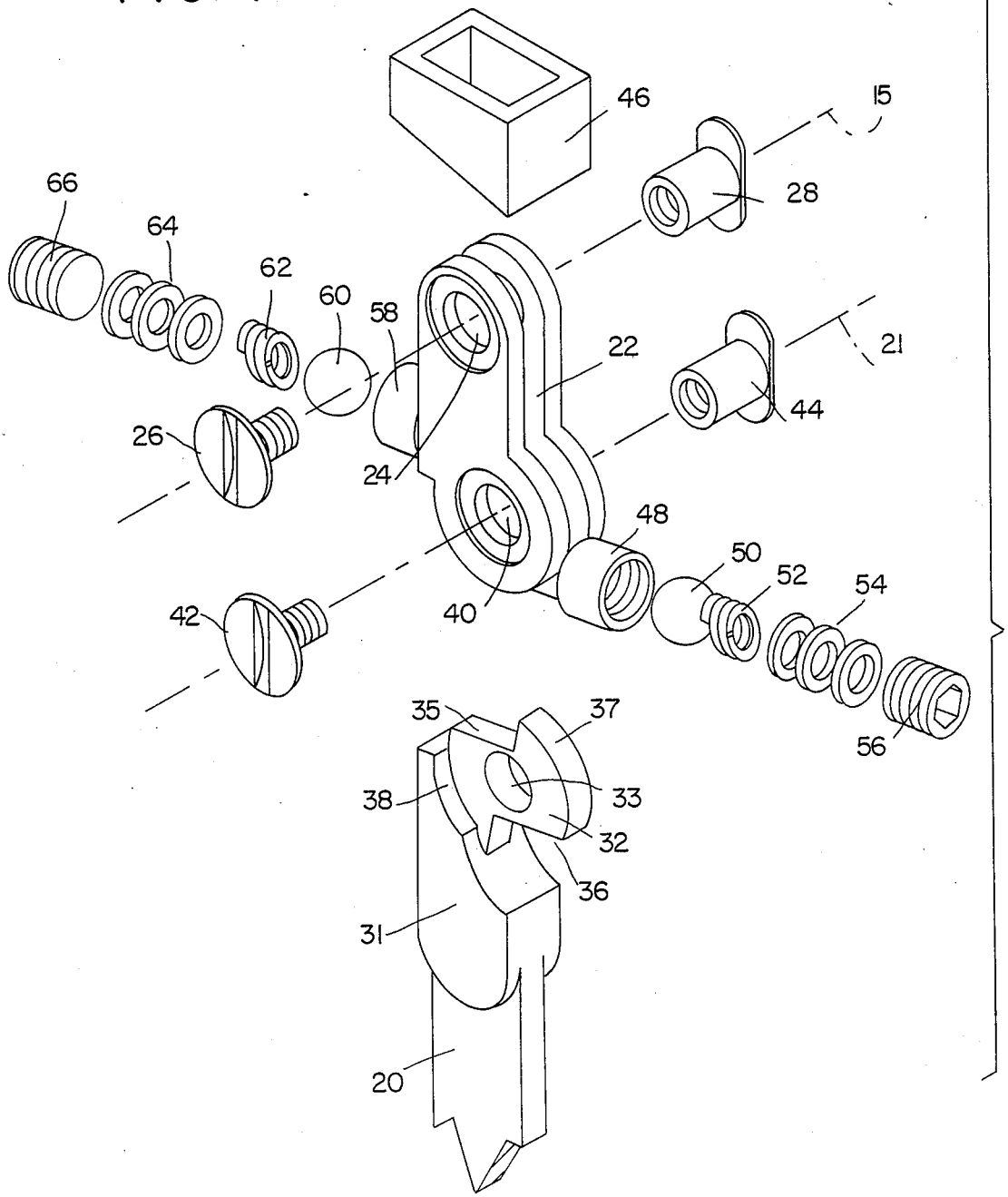
FIG. 1 is an exploded view of the inventive brace.
Figure 2:
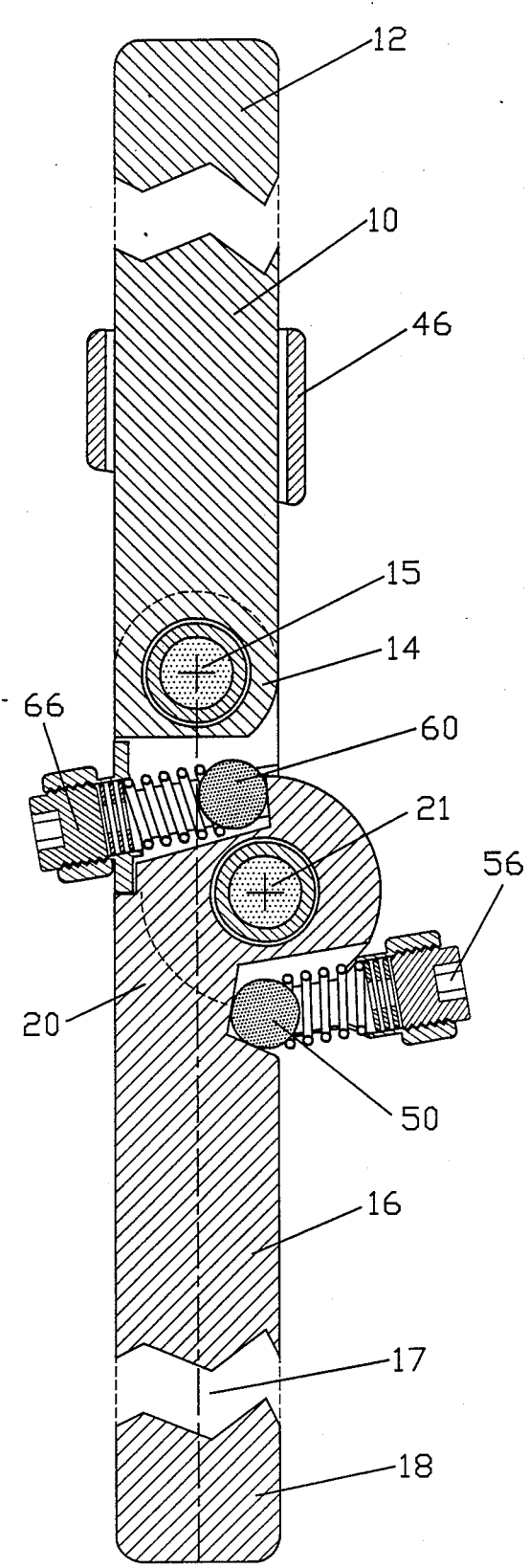
FIG. 2 is a longitudinal cross-sectional schematic view of the inventive brace, having the lower member thereof in co-linear alignment with the upper member thereof.

With reference to the exploded view of FIG. 1 and the longitudinal cross-sectional view of FIG. 2, the inventive knee brace is seen to include an upper support member 10 for support of a lateral side of the leg above the knee thereof. Said upper member includes an upper end 12 and lower end 14 in which is provided a circular opening 15.

The inventive brace also includes a lower support member 16 for the support of said lateral side of the leg, but below the knee thereof. Said lower support member 16 includes a lower end 18 and an upper end 20, said upper end including an enlarged portion 31 and projecting element 32 which is characterized by a curved line of dependency 38 with said portion 31. Radially opposite thereto is curved surface 37. It is also noted that said element 32 possesses said circular opening 33 and, thereabove, exhibits a transverse flat surface 35 and, therebelow, a transverse flat surface 36.

Further shown in FIGS. 1 and 2 is a bi-axial element 22 having a primary axis 15 and a secondary axis 21. As may be noted, said lower end 14 of said upper member 10 is rotationally coupled to said primary axis 15 through the use of a bolt 26 which passes through hole 15 of said lower end 14, and hole 24 of said bi-axial element 22, to achieve a thread-fit connection into threaded nut 28.

Further, upper end 20 of lower support member 16 is rotationally coupled to secondary axis 21, this being achieved through the passage of bolt 42 through hole 33 of enlarged portion 31 of said end 20, and through hole 40 of bi-axial element 22 to achieve a thread-fit connection into threaded nut 44 to thereby control the motion of upper member 10 relative to the bi-axial element 22. There is also provided drop locking means 46 which is proportioned for slide-fit advancement and retraction over lower end 14 of upper member 10 to selectively reach the position shown in FIG. 3. When said locking means has achieved the position of FIG. 3, said end 14 of upper member 10 is rigidly coupled to the upper portion of the bi-axial element 22 such that upper member 10 cannot rotate relative thereto. Accordingly, the locked position of FIG. 3 would be not employed when the user of the inventive brace system wishes to sit down.

Figure 3:
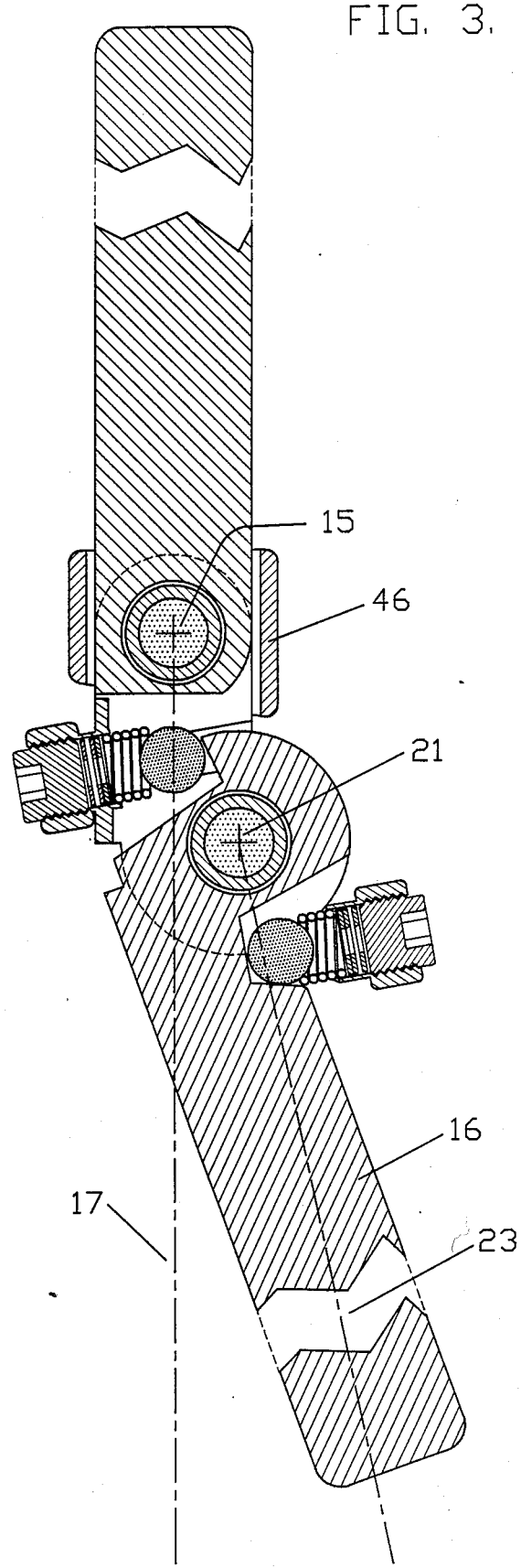
FIG. 3 is a view, similar to the view of FIG. 2, however showing the lower member thereof in rotation about the secondary axis of the brace.

By locking upper member 10 to the upper portion of bi-axial element 22, the primary axis 15 and its radius of rotation 17 (see FIG. 2) is abrogated and is replaced by secondary axis 21 and its radius of rotation 23 (See FIG. 3). Such selective overriding of the rotational coupling between upper member 10 and the primary axis 15 is therefore most useful to a user of the inventive system when the user wishes to change the operational axis of the system from the primary axis 15 to the secondary axis 21.

Also shown in the views of FIGS. 1, 2 and 3 are first and second mechanical damping means. Said first mechanical damping means comprises a collar 48 formed integrally with a lower end of bi-axial element 22, a ball bearing 50, a spring 52, washers 54, and an Allen-head nut 56. The second mechanical damping means comprises collar 58 which depends from a center area of bi-axial element 22, a ball bearing 60, a spring 62, washers 64, and an Allen-head nut 66. As may be appreciated from the views of FIGS. 2 and 3, the function of said mechanical damping means is to apply a selective amount of spring force parallel to said transverse surfaces 35 and 36 of projecting element 32 and, specifically, in the direction of said curved surfaces 37 and 38 of said enlarged portion 31. Accordingly, the result of the application of said spring forces is to control the characteristic of the rotational coupling between said secondary axis 21 and said upper end 20 of said lower member 16. More particularly, by the use of compression springs 52 and 54, and their force-control means comprising Allen-head nuts 56 and 66 respectively, the spring forces of both of said damping means are applied in the same direction of rotation relative to said secondary axis, i.e., in a clockwise direction relative to said axis in the views of FIGS. 2 and 3. However, the spring forces are thereby also applied in directions which are opposing to each other when viewed relative to the plane of the radius of rotation 23 of the secondary axis 21. The effect of this arrangement of parts is to provide a brace having a lower member which exhibits a more natural flexibility and resilience from the knee downward. As may be noted, when drop lock means 46 is not actuated, relatively little force will be applied in the direction of the axis of springs 52 and 62. Thereby, the action of the primary axis 15 will predominate over that of the secondary axis 21, and the radius of rotation 17 of the primary axis 15 will dominate the behavior of the system. This is a preferred situation when the knee of the wearer of the brace is in a bent situation, however, when the wearer is walking or otherwise moving, it is desirable for the secondary axis 21, and its associated mechanical damping means, to predominate so that the user of the brace will be provided with a flexibility and resilience of the lower member of brace 16 that will approximate that of the natural knee and lower leg.

Figure 4:
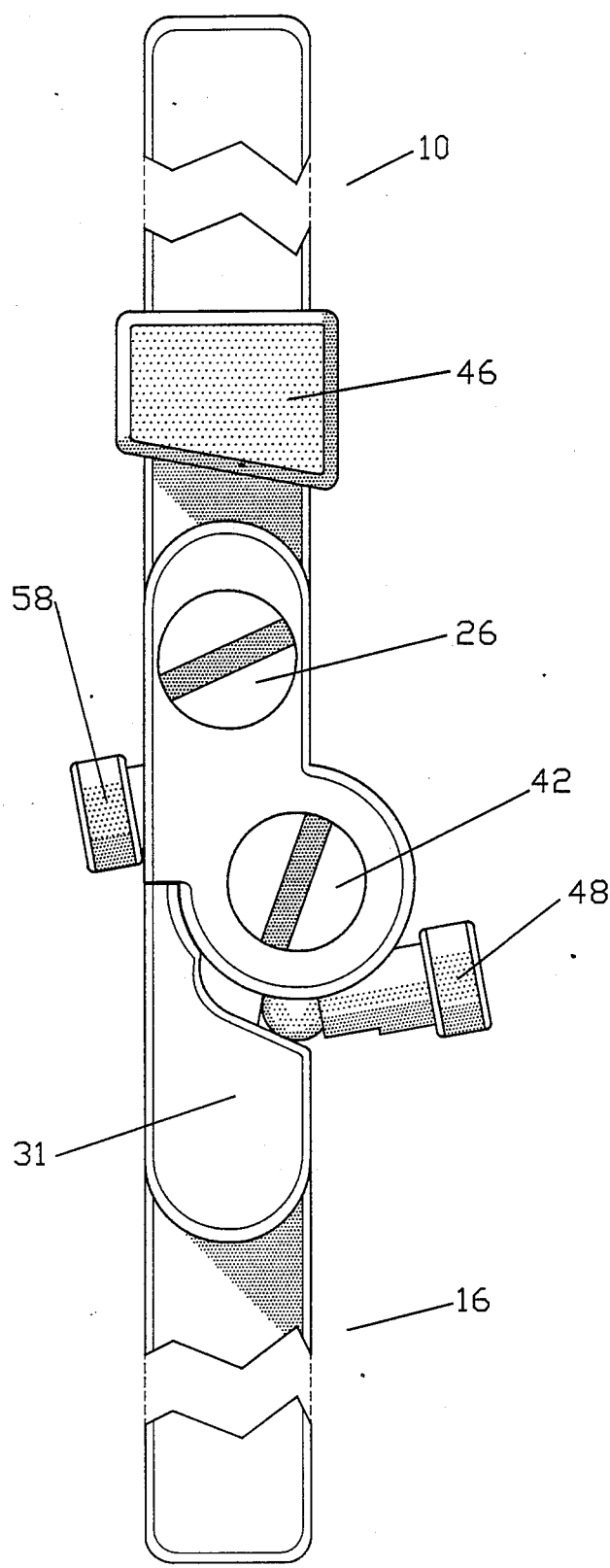
FIG. 4 is an external front elevational view of the brace having the lower member in co-linear alignment with the upper member thereof.
Figure 5:
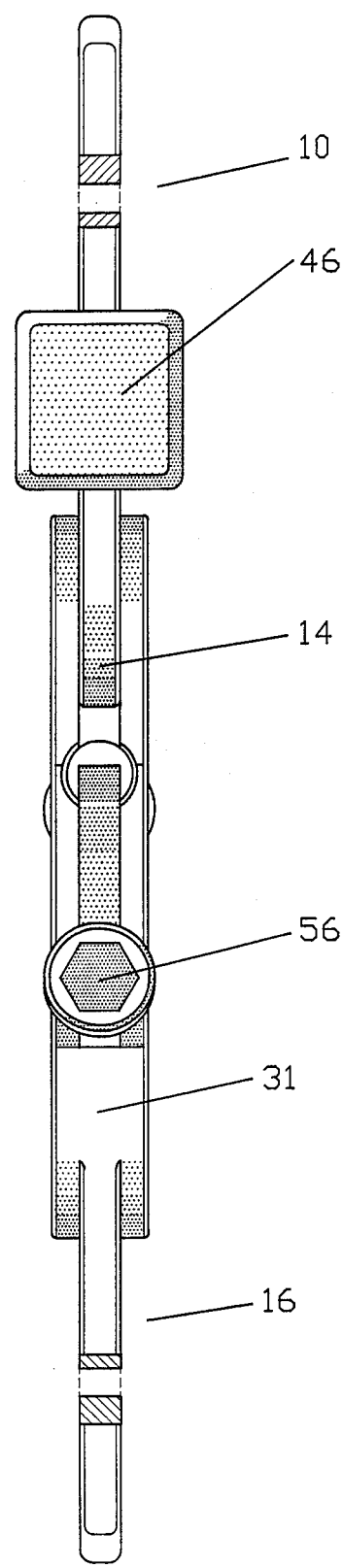
FIG. 5 is a side view of the view of FIG. 4.

The views of FIGS. 4 and 5 show the external appearance of the system and the ease of accessibility to the user of bolts 26 and 42 for the purpose of tightening the rotational characteristic of axis 15 and 21, respectively. Said figures also show the accessibility to collars 48 and 58 for purposes of tightening or loosening respective Allen-head nuts 56 and 66 to selectively increase or decrease the spring force of said damping means applied, as above described, against said secondary axis 21.

Accordingly, while there has been shown and described a preferred embodiment of the present invention, it is to be appreciated that the invention may be embodied other than is herein specifically shown and described and that, within said embodiment, certain changes may be made without departing from the underlying idea or principles of this invention within the scope of the appended claims.

Having thus described my invention, what I claim as new, useful, and non-obvious and, accordingly, secure by Letters Patent of the United States is:

1. A knee brace having a primary joint and a flexible secondary joint, the brace comprising:
   (a) an upper member for the support of a lateral side of a leg above the knee thereof, said upper member having an upper end and a lower end;
   (b) a lower means for the support of said lateral side of the leg below the knee thereof, said lower member having an upper end and a lower end;
   (c) a bi-axial element having a primary axis and a second axis, said lower end of said upper member being rotationally coupled to said primary axis, said upper end of said lower member being rotationally coupled to said secondary axis;
   (d) lock means for selectively locking said lower end of said upper member to said primary axis, thereby selectably overriding said rotational coupling between said upper member and said primary axis of said bi-axial element, in which actuation of said locking means operates to change the effective axis of said bi-axial element from said primary axis to said second axis; and
   (e) mechanical damping means oriented in said bi-axial element and applied against said secondary axis, said damping means comprising means for angularly biasing said secondary axis relative to said primary axis in a direction of rotation anterior to said primary axis,
   whereby said knee brace will permit a more natural flexibility of the knee and of the lower leg, both when the knee is straight and when the knee is bent as is the case during sitting.

2. The system as recited in claim 1, which said mechanical damping means comprises:
   a pair of compression-adjustable spring assemblies each positioned to apply its spring force in the same direction as the direction of the rotation of said secondary axis, but to apply the spring force of said spring assemblies in opposing directions relative to the plane of a radius of rotation of said secondary axis.

3. The brace as recited in claim 2, in which said lock means comprises a slip element proportioned to peripherally engage both said lower end of said upper member and said primary axis of said bi-axial element.

4. The brace as recited in claim 3, in which said damping means comprising springs and ball bearings said bearings, comprising interface means between an inner end of each said springs and said upper end of said lower member.

5. The brace as recited in claim 4, in which said spring assemblies comprise Allen-head screw nuts at both outer ends of said spring assemblies wherein upon the rotational advancement of said Allen-head screw nuts, an increase of the compression of the springs of said spring assemblies will occur.

* * * * *